(12) United States Patent
Mandica et al.

(10) Patent No.: US 10,729,899 B2
(45) Date of Patent: Aug. 4, 2020

(54) DEVICE FOR APPLYING A PRODUCT TO BE DISTRIBUTED ON THE SKIN OF A USER BY IONTOPHORESIS

(71) Applicant: SEB S.A., Ecully (FR)

(72) Inventors: Franck Mandica, Francheville (FR); Johan Sabattier, Mornant (FR)

(73) Assignee: SEB S.A., Ecully (FR)

( * ) Notice: Subject to any disclaimer, the term of this patent is extended or adjusted under 35 U.S.C. 154(b) by 0 days.

(21) Appl. No.: 15/773,931

(22) PCT Filed: Nov. 4, 2016

(86) PCT No.: PCT/FR2016/052868
§ 371 (c)(1),
(2) Date: May 4, 2018

(87) PCT Pub. No.: WO2017/077255
PCT Pub. Date: May 11, 2017

(65) Prior Publication Data
US 2018/0318580 A1 Nov. 8, 2018

(30) Foreign Application Priority Data
Nov. 6, 2015 (FR) .................................. 15 60679

(51) Int. Cl.
*A61N 1/04* (2006.01)
(52) U.S. Cl.
CPC ......... *A61N 1/0448* (2013.01); *A61N 1/0428* (2013.01)

(58) Field of Classification Search
CPC ........ A61M 35/003; A61M 2037/0007; A61M 2205/055; A61N 1/0428; A61N 1/0432;
(Continued)

(56) References Cited

U.S. PATENT DOCUMENTS 5,911,223 A * 6/1999 Weaver ................ A61N 1/0424
128/898
6,708,060 B1 * 3/2004 Avrahami ................ A61N 1/30
600/372
(Continued)

FOREIGN PATENT DOCUMENTS

EP    0 942 278 A2    9/1999
FR    2 619 308 A1    2/1989
(Continued)

OTHER PUBLICATIONS

International Search Report as issued in International Patent Application No. PCT/FR2016/052868, dated Feb. 3, 2017.
(Continued)

*Primary Examiner* — Shefali D Patel
(74) *Attorney, Agent, or Firm* — Pillsbury Winthrop Shaw Pittman LLP

(57) ABSTRACT

A device for applying a product to be distributed on user's skin by iontophoresis, includes a body intended to receive the product to be distributed, including an electric current generator; and an applicator head mounted on the body, the applicator head including: a device for distributing the product to be distributed on the skin; and a first electrode and a second electrode that are separated by an interelectrode zone, the first electrode and the second electrode to receive an electric current from the generator.

18 Claims, 4 Drawing Sheets

(58) Field of Classification Search
CPC ........ A61N 1/0448; A61N 1/30; A61N 1/303; A61N 1/325
See application file for complete search history.

(56) References Cited

U.S. PATENT DOCUMENTS

| | | | |
|---|---|---|---|
| 7,062,317 B2 * | 6/2006 | Avrahami | A61M 37/0015 604/20 |
| 7,083,580 B2 * | 8/2006 | Bernabei | A61H 7/008 601/15 |
| 7,522,954 B2 * | 4/2009 | Tedoldi | A61N 1/044 604/20 |
| 2002/0161323 A1 | 10/2002 | Miller et al. | |

FOREIGN PATENT DOCUMENTS

| | | |
|---|---|---|
| FR | 2 980 370 A1 | 3/2013 |
| WO | WO 02/085451 A2 | 10/2002 |

OTHER PUBLICATIONS

International Preliminary Report on Patentability and the Written Opinion of the International Searching Authority as issued in International Patent Application No. PCT/FR2016/052868, dated May 8, 2018.

* cited by examiner

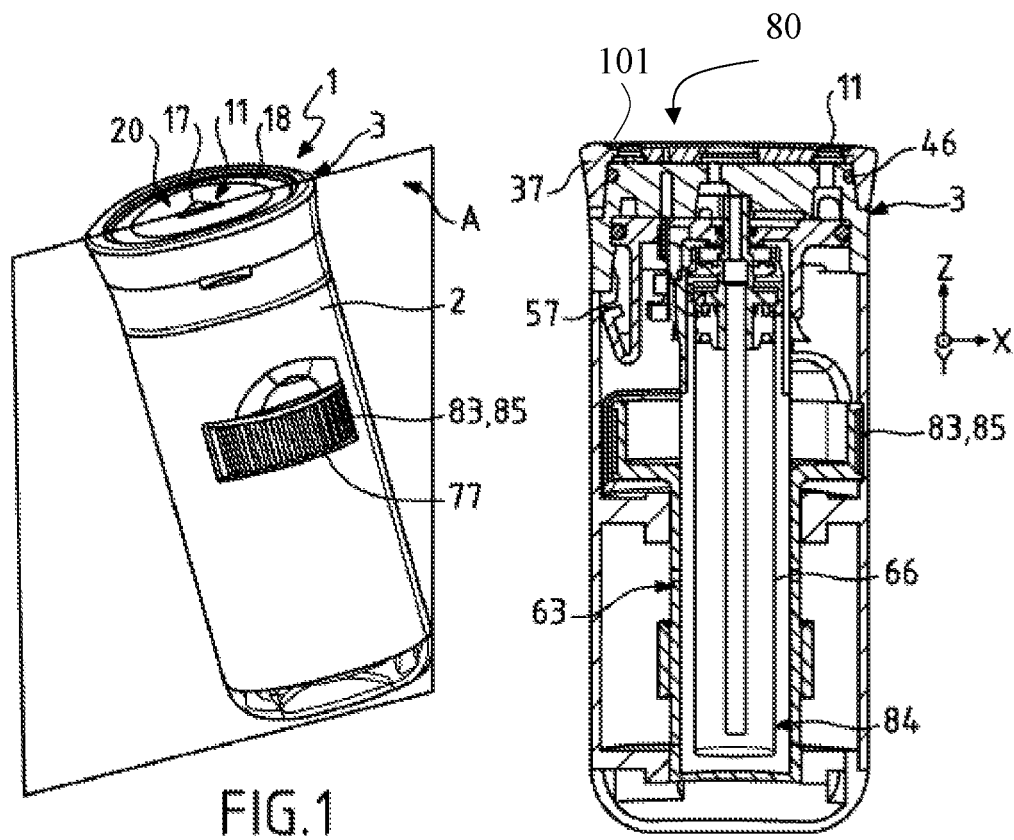
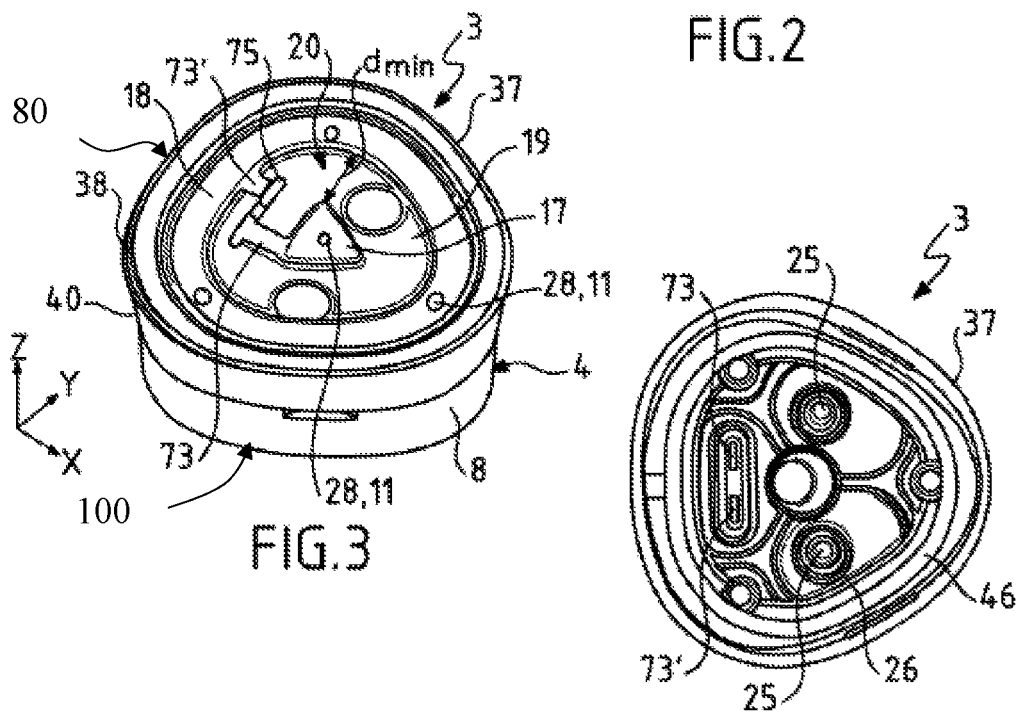

DEVICE FOR APPLYING A PRODUCT TO BE DISTRIBUTED ON THE SKIN OF A USER BY IONTOPHORESIS

CROSS-REFERENCE TO RELATED APPLICATIONS

This application is the U.S. National Stage of PCT/FR2016/052868, filed Nov. 4, 2016, which in turn claims priority to French patent application number 1560679 filed Nov. 6, 2015. The content of these applications are incorporated herein by reference in their entireties.

1. FIELD OF THE INVENTION

This invention concerns the field of devices permitting the application of a cosmetic or therapeutic product to be distributed on the skin of a user. In particular, it deals with devices using the principle of iontophoresis to improve the delivery of a product's active ingredient through the different skin layers.

2. PRIOR ART

We know of a device for applying a product to be distributed on the skin by iontophoresis intended to improve the delivery of a product's active ingredient through the skin. Such a device is known from the document FR 2,619,308 which comprises a body and an applicator head fixed to the said body. The body houses a reservoir for the product to be applied, an electric current generator and one first and one second electrode receiving an electric current from the current generator. The first electrode covers a wall of the body, while the second electrode is in permanent contact with the product contained in the reservoir. The applicator head comprises a soleplate equipped with housings in which each housing receives a ball and which cooperates with the product reservoir.

One of the problems connected to this device for applying product to be distributed is that the first electrode is situated on the surface of the device body and that the second electrode is located in the reservoir close to the applicator head, which creates leakage currents between the first and second electrodes. These leakage currents principally go through the product because of the presence of the second electrode in the reservoir, which implies that a very weak current crosses the skin to permit the product and its active ingredients to penetrate through the skin.

3. OBJECTIVES OF THE INVENTION

In particular, the invention aims to remedy all or a portion of the drawbacks of the prior art.

One objective of the invention is to provide a device for applying a product to be distributed by iontophoresis on the skin of a user that permits leakage currents in the reservoir containing the product while being compact and simple to manufacture.

4. SUMMARY OF THE INVENTION

These objectives are achieved through a device for applying a product to be distributed on the skin of a user by iontophoresis and comprising:
 a body intended to receive the product to be distributed and comprising an electric current generator; and,
 an applicator head mounted on the body, the applicator head comprising:
  at least one means for distributing the product to be distributed on the skin; and
  at least one first and one second electrode separated by an inter-electrode zone, the first and second electrodes receiving an electric current from the said generator.

This solution permits solving the aforementioned problems. In particular, such a configuration of the application device yields a compact, simple device that is easy to handle and use. In addition, having the first and second electrodes placed in the applicator head makes it possible, on the one hand, to reduce the distance between the first and second electrodes, resulting in the application of a lower intensity current, and on the other hand, to control the path of the current and the penetration of the active ingredients through the user's skin. As such, it is possible to target the skin zone to be treated and limit the leakage currents.

Advantageously, the applicator head is removable in relation to the body, so as to enable cleaning or replacement of defective parts.

According to a characteristic of the invention, the applicator head comprises at least one distribution cavity.

According to an advantageous characteristic, but optionally, the first and second electrodes are situated in the same plane.

More precisely, the inter-electrode zone is situated in a plane parallel to the said plane of the first and second electrodes, the plane of the first and second electrodes and the plane of the inter-electrode zone being situated at a predetermined distance from each other. In this way, arranging the first and second electrodes set back from the inter-electrode zone avoids direct contact of the electrodes with the user's skin, which prevents irritation or electrical tingling. This permits reducing the quantity of product that can remain/accumulate between the plane of the first and second electrodes and the plane of the inter-electrode zone. In addition, this configuration makes it possible to promote the passage of current in the skin and not through the formula situated on the plane of the first and second electrodes for iontophoresis.

Advantageously, but optionally, the predetermined distance between the plane of the first and second electrodes and the plane of the inter-electrode zone is between 0.3 and 1.3 mm.

According to an advantageous configuration, but not exclusively, the inter-electrode zone comprises an application surface intended to be in contact with the user's skin. This configuration also prevents the formation of a thick film of product between the first and second electrode where the electric current would then preferentially circulate.

According to another characteristic of the invention, the inter-electrode zone presents a predetermined minimum distance between the first electrode and the second electrode. This predetermined minimum distance may be between 5 and 20 mm. This arrangement permits, on the one hand, determining the treatment zone and in particular the depth of penetration of the current and of the active ingredients in the user's skin.

According to another characteristic of the invention, the applicator head comprises a distribution circuit containing distribution channels distributing the product toward the product distribution means.

According to another characteristic of the invention, the first electrode and the second electrode are arranged downstream from the distribution circuit. Thus, the product is distributed to the right of the first and second electrodes so as to optimize the quantity of the product's active ingredient conducted in the treatment zone of the user's skin.

According to a characteristic of the invention, the first electrode and the second electrode each comprise a wall with perforations so as to permit the product to circulate toward the user's skin.

According to one embodiment, the distribution means comprises one or more outlet openings, the perforations of the first and second electrodes may comprise the one or more product outlet openings toward the user.

According to another embodiment, a plate with perforations may be arranged in the applicator head, the distribution means comprising one or more outlet openings and the perforations constituting the one or more product outlet openings toward the user's skin.

According to an embodiment of the invention, the product may be contained in a cartridge removably connected to the body of the device. Arranging the product to be distributed in a cartridge makes refilling easy and simple. Also, different types of products with cosmetic and therapeutic applications may be used with the application device without having to clean the body with each use. In addition, the cartridge permits controlling the distribution of the product on the user's skin.

According to a characteristic of the invention, the body may comprise at least one means for extracting the product from the body toward the applicator head. In particular, this extraction means may be operated manually or by motor.

According to a characteristic of the invention, the applicator head comprises an electrical insulation means which is fluidically interposed between the first electrode and the second electrode, the said electrical insulation means being configured so as to permit or prevent the passage of electric current from the first and second electrodes to the body. This arrangement also permits limiting the leakage currents between the body and the first and second electrodes. The application device is therefore safer and more effective for the user.

According to a characteristic of the invention, the electrical insulation means is able to be in:
- a closed position in which current circulates only between the first and second electrodes; or,
- an open position in which current circulates between the first and second electrodes and in the distribution channels of the applicator head.

As such, this configuration permits controlling the circulation of the product and in particular that of the current in the device body and in particular in the product which is conductive in order to avoid leakage currents.

According to another characteristic of the invention, the electrical insulation means is in the open position when a pressure inside the electrical insulation means reaches a predetermined threshold. As such, when it is not necessary to supply product (product available in the head's distribution cavity), there is no circulation of current. In addition, this permits putting the product to be distributed under pressure when the product has to supply the cavities, which helps it fill the distribution cavities.

According to another characteristic of the invention, the electrical insulation means is arranged on one of the distribution channels leading to the first electrode. Such a configuration makes it possible to prevent the current lines from passing from the first electrode to the second electrode inside the applicator head and to prevent the passage of current to the body.

According to another embodiment, the first electrode is arranged at the center of the head and the second electrode is arranged toward the periphery of the head, in order to facilitate the mounting and assembly of the applicator head.

Advantageously but not restrictively, the insulation means is a valve. The valve makes it possible to simply and effectively permit or stop the circulation of a fluid, while being watertight.

According to another embodiment, the application device may comprise a temperature probe installed in the head. This probe permits monitoring the user's skin temperature in order to avoid injuries that may occur when the current intensity is too high.

5. LIST OF FIGURES

Other innovative characteristics and advantages will be seen in the following description, provided for reference and in no way restrictive, in reference to the attached drawings, in which:

FIG. 1 is a perspective view of a device for applying a product to be distributed on a user's skin by iontophoresis according to the invention;

FIG. 2 is a longitudinal cross-sectional view of the product application device according to the cutting plane A-A in FIG. 1.

FIG. 3 is a top perspective view of an example of an applicator head of a product application device according to the invention;

FIG. 4 is a bottom view of the example of the applicator head illustrated in FIG. 3;

Figure 8:
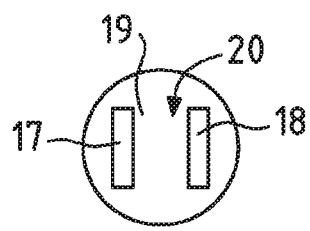
Figure 9:
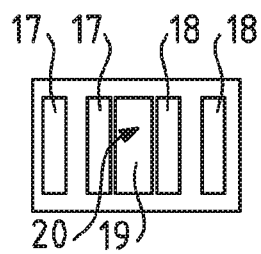
Figure 10:
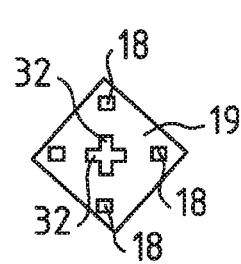
Figure 11:
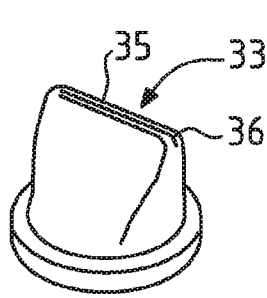
Figure 12:
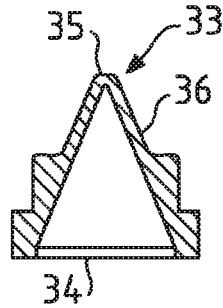
Figure 13:
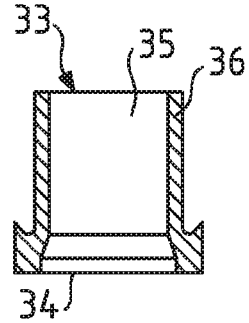
Figure 14:
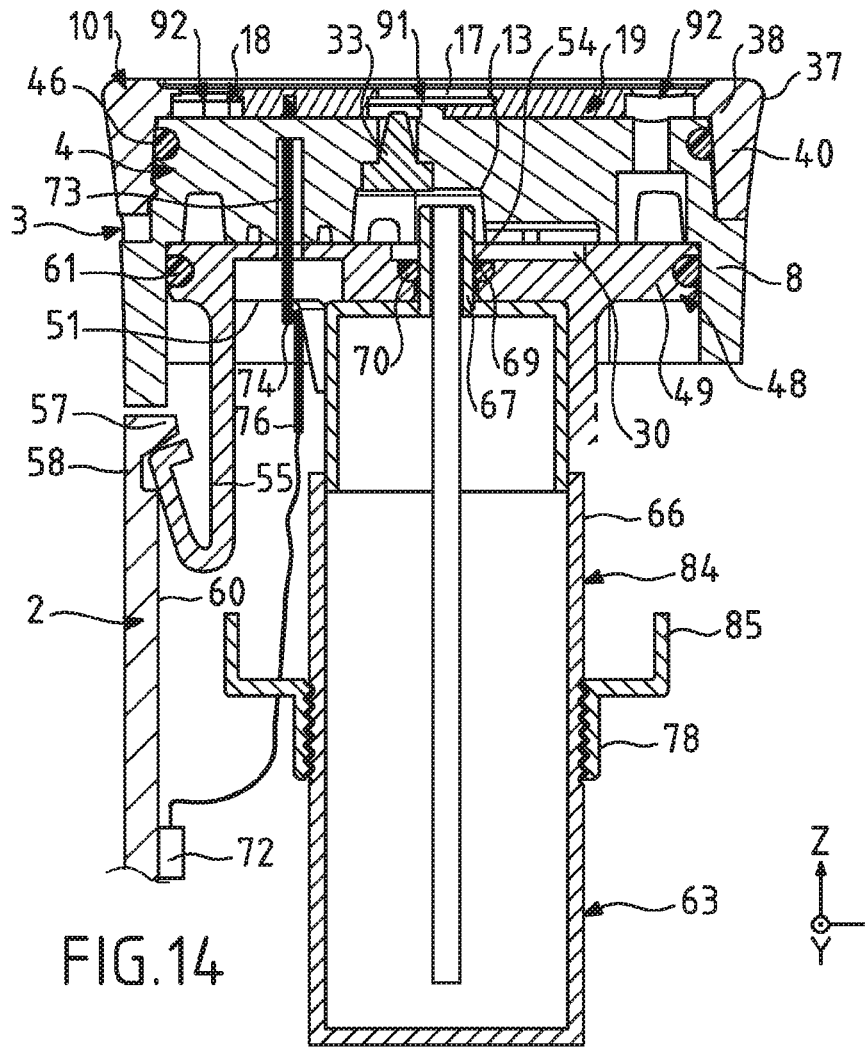
Figure 15:
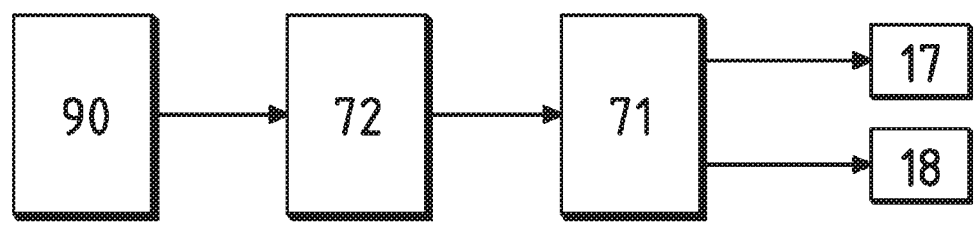
Figure 16:
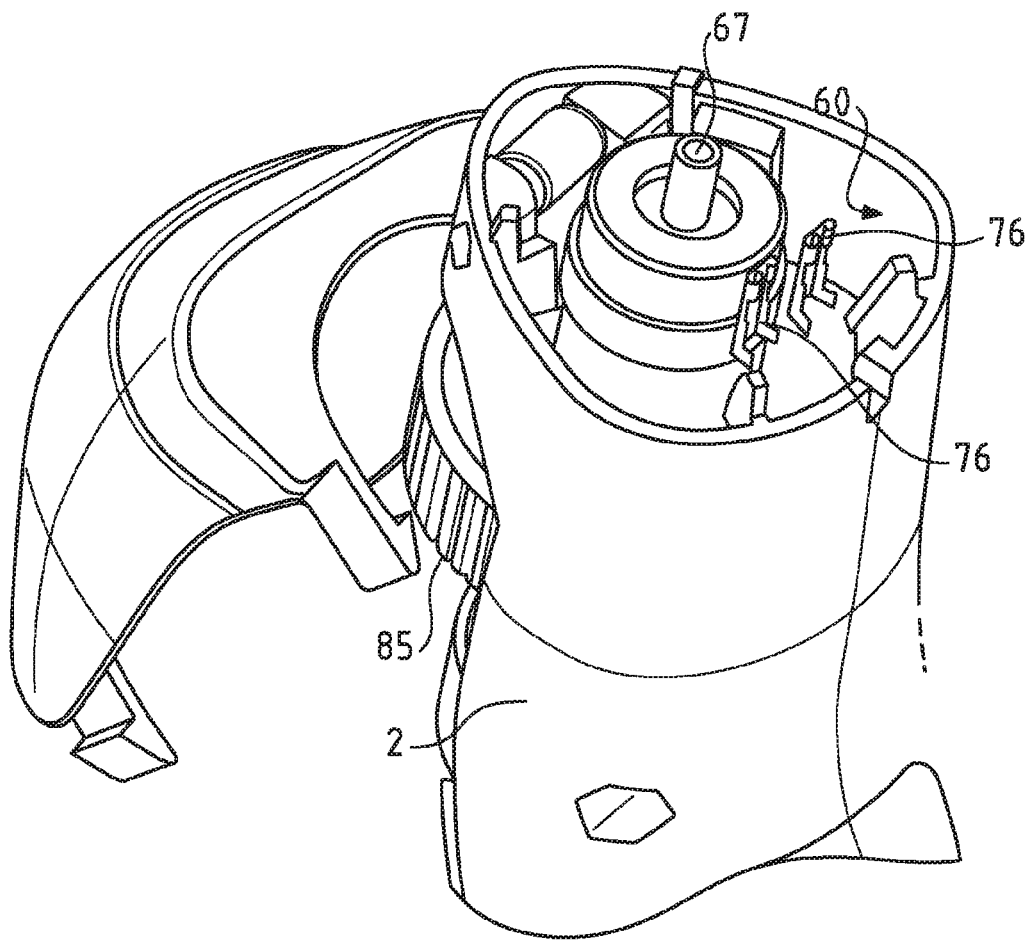

FIGS. 8 to 10 schematically represent embodiments of the arrangement of the first and second electrodes in the applicator head; and FIGS. 11 to 13 represent an example of electrical insulation means to be interposed between the first electrode and the second electrode;

FIG. 14 is a partial sectional and detail view of an example of an applicator head mounted and connected on an application device body which includes a cartridge according to the invention;

FIG. 15 is a block diagram representing the electrical communications between an electronic control circuit, a current generator and the first and second electrodes; and FIG. 16 illustrates a top perspective view of a connection portion of the device body intended to connect with an applicator head according to the invention.

6. DETAILED DESCRIPTION

In reference to FIG. 1, the device 1 for applying a product to be distributed on a user's skin by iontophoresis according to the invention is intended for cosmetic and/or therapeutic treatment of the user's skin. The device 1 here uses the principle of iontophoresis, an electrophoresis principle, to promote and facilitate the penetration of the product and its active ingredients through the user's skin. Iontophoresis here is the application of an electric field through the skin acting as a driving force to permit the displacement of the product's ions. The skin is treated in a non-invasive manner.

The device comprises a body 2 forming a gripping device of the device 1 and an applicator head 3 mounted on the body 2. As visible in FIG. 2, the device comprises at least one means 84 for storing the product to be distributed on the skin. Advantageously, but not restrictively, the body 2 comprises the means 84 for storing the product to be distributed. As for the applicator head 3, it comprises at least one means 11 for distribution of the product to be distributed on the user's skin.

The term "product" within the meaning of the invention refers to a product in the form of a fluid such as a liquid and/or an aqueous composition.

In reference to FIGS. 2 to 7, the applicator head 3 is removably mounted on the body 2 so as to permit replacement of the head in the event of deterioration and/or damage, and thus to facilitate its cleaning. The applicator head 3, as illustrated in FIGS. 2, 3 and 4, comprises an upper interface 80 that includes upper surface 101 (see FIGS. 2 and 14) intended to be oriented toward the user's skin and an opposite lower interface 100 intended to be connected to the body 2 of the product application device.

To facilitate comprehension of the invention, we consider that the applicator head 3 extends along a vertical longitudinal axis Z. A horizontal axis X is also represented, which is perpendicular to the vertical longitudinal axis Z and a transverse axis Y such that these three axes X, Y, Z form a right-handed coordinate system as illustrated in FIGS. 2 and 3, for example. The terms "lower," "upper," "high," "low," "top," and "bottom" are defined with reference to the vertical longitudinal axis Z and the term "lateral" is defined with reference to the horizontal axis X.

Figure 5:
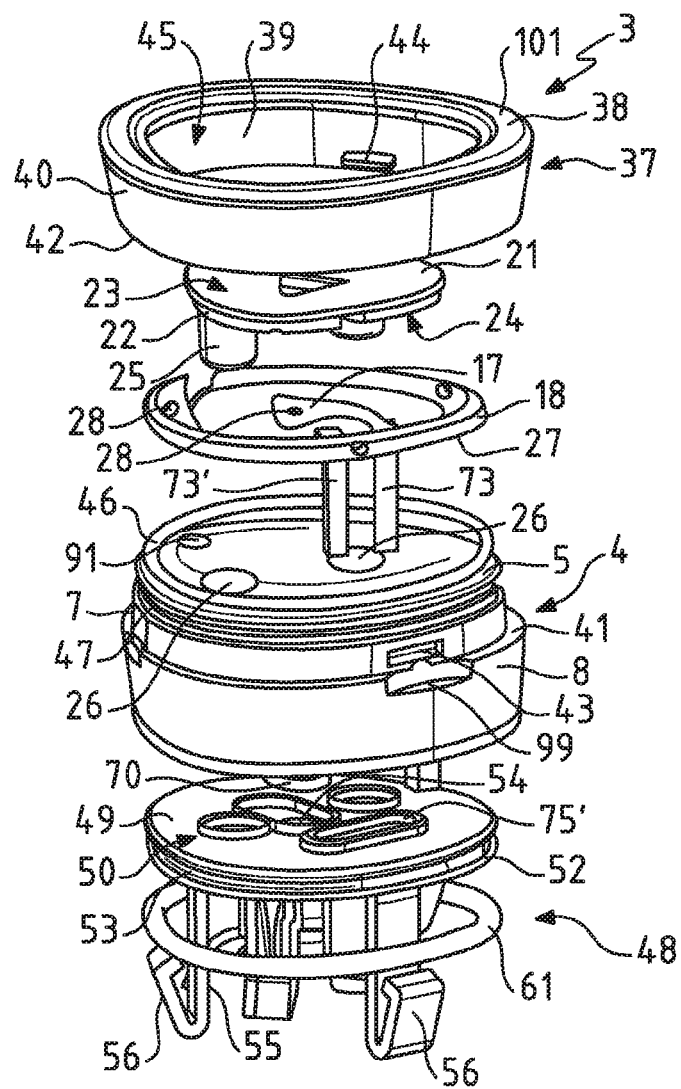
FIG. 5 is an exploded perspective view of an example of an applicator head of an application device according to the invention.
Figure 6:
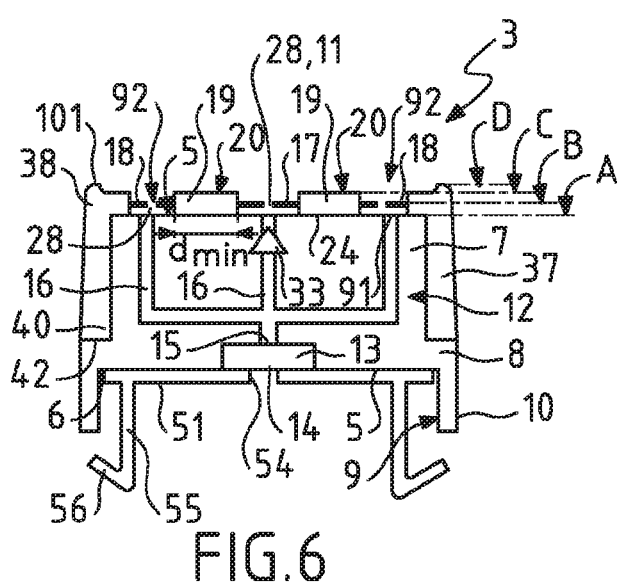
FIGS. 6 and 7 illustrate schematically and in more detail a sectional view of two examples of applicator head according to the invention.
Figure 7:
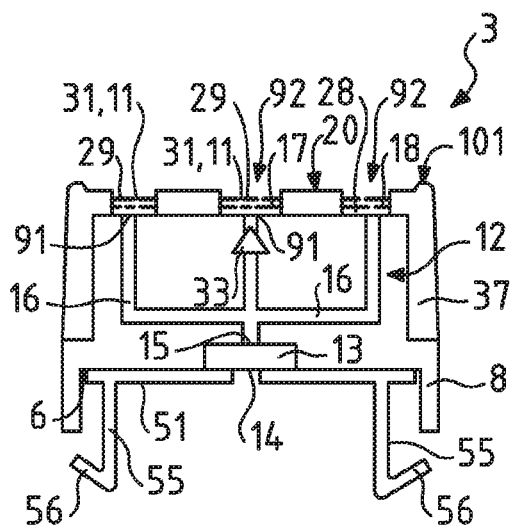

Illustrated more precisely in FIGS. 5, 6 and 7, the applicator head 3 comprises a base 4 comprising an upper surface 5 and a lower surface 6 connected by a wall 7. This wall 7 is extended by a side skirt 8 which extends toward the bottom, according to the axis Z, from the periphery of the wall 7. The side skirt 8 has an inner surface 9 and an opposite outer surface 10 along its length. The base 4 has a roughly triangular cross-section. Of course, the base 4 may have a circular or other cross-section when compatible with the body of the application device 1.

On FIGS. 6 and 7, the base 4 also comprises a circuit 12 for distribution of the product to be distributed arranged between the upper surface 5 and the lower surface 6. In particular, the distribution circuit 12 comprises, at the lower surface 6 of the base 4, a buffer reservoir 13 intended to receive or collect the product from the body 2 of the application device 1. The buffer reservoir 13 has an inlet 14 receiving the product to be distributed from the body 2 and an outlet 15 permitting the product to circulate toward the means 11 for distribution of the product on the skin. To permit the product to circulate toward the distribution means 11, the distribution circuit 12 comprises distribution channels 16 connecting the means 11 for distribution of the product and the buffer reservoir 13. The distribution channels 16 are formed in the wall 7 of the base 4. The distribution channels end at the upper surface 5 of the base 4 with distribution openings 91 and in particular they permit connecting the outlet 15 of the buffer reservoir 13 with these distribution openings 91. Advantageously, but not restrictively, each distribution opening 91 communicates fluidically with a distribution channel 16 of the distribution circuit 12.

The application device comprises at least a first electrode 17 and at least a second electrode 18 for iontophoresis. These first and second electrodes 17, 18 are each installed in at least one distribution cavity 92 contained by the application device 1 and able to receive the product to be distributed. In particular, the distribution cavity 92 is formed in the applicator head 3 and is in fluidic communication with at least one distribution opening 91. We observe more precisely on FIGS. 6 and 7 that the first electrode 17 and the second electrode 18 are arranged over the upper surface 5 of the base 4. The first electrode 17 and the second electrode 18 are connected to an electric current generator (described later in the description) so as to produce an electric current which is intended to cause the penetration of the product to be distributed in the skin. The first electrode 17 and the second electrode 18 for iontophoresis are separated from each other by an inter-electrode zone 19 ensuring a constant space between the first and second electrodes 17, 18. The inter-electrode zone 19 comprises an application surface 20 intended to be in contact with the skin in order to apply the product to be distributed. More precisely, the inter-electrode zone 19 is advantageously, but not restrictively, formed by an assembly member having a base 21 with a side wall 22 connecting a first surface 23 oriented toward the user's skin, which thus defines the application surface 20 and a second surface 24 which is opposite it. The assembly member here has two pins 25 which extend from the second surface 24 and which are intended to fit into two corresponding holes 26 of the base 4 so as to permit the assembly member to fit into the base 4. The holes 26 cross the base 4 from the upper surface 5 to the lower surface 6 of the base 4 (see FIG. 4). Since the side wall 22 has a certain thickness, the application surface 20 is situated at a distance from the upper surface 5 of the base 4. In particular, the upper surface 5 of the base 4 is defined in a plane A, while the first and second electrodes 17, 18, being arranged over the upper surface 5, are defined in a plane B parallel to the plane A. As for the inter-electrode zone 19, and in particular, the application surface 20, this is defined in a plane C which is parallel to the plane B of the first and second electrodes 17, 18. In other words, the first and second electrodes 17, 18 are set back from the said inter-electrode zone 19, so that the said first and second electrodes are not in contact with the user's skin. The plane B of the first and second electrodes 17, 18 and the plane C of the inter-electrode zone 19 are situated at a predetermined distance from each other. The predetermined distance is between 0.3 and 1.3 millimeters (mm). According to a particular characteristic of the invention, the inter-electrode zone 19 has a predetermined minimum distance dmin between the first electrode 17 and the second electrode 18 which is between 5 and 20 mm. Preferably, but not restrictively, this minimum distance dmin is 10 mm. The distribution cavity 92 is thus obtained because of the distance separating the planes B, C from the first and second electrodes 17, 18 and from the inter-electrode zone 19. The latter therefore has at least one bottom formed by the upper surface 5 of the base 4 and the side walls formed by the side wall 22 of the assembly member (inter-electrode zone 19). The side walls of the cavity 92 may also be formed of an inner wall of a collar 38 of a cap 37 contained by the applicator head 3 described below. The cavity 92 of the applicator head 3 permits the formation of a thin film of product to be distributed in this cavity 92. In other words, the accumulation of product is avoided on the upper interface of the applicator head.

Advantageously, but not restrictively, the distribution means 11 comprises one or more product outlet openings toward the user's skin, ending at the upper interface of the applicator head 3.

According to a characteristic of the invention, the first electrode 17 and the second electrode 18 each have a wall 27 with perforations 28.

According to a first embodiment illustrated in FIG. 6, the perforation or perforations 28 distribute the product toward the user's skin. In other words, the perforations 28 constitute the one or more product outlet openings toward the skin. Thus, the product circulates through the distribution opening 91 of the base 4 toward the perforations 28 of each first and second electrode 17, 18. In this embodiment, the first and second electrodes are made of an electrically conductive material. This electrically conductive material may comprise a metallic material or a polymer or a composite material containing this polymer material. The polymer may be a polytetrafluoroethylene (PTFE). The metallic material may be a stainless steel.

According to a second embodiment illustrated in FIG. 7, at least one plate 29 presenting a wall with perforations 31 is arranged in the applicator head 3 of the application device 1. More precisely, the plate 29 is arranged above each first and second electrode 17, 18. In this case, the product circulates through the one or more distribution openings 91, the one or more perforations 28 of the first and second electrodes 17, 18 toward the perforations 31 of the plate 29, which distribute the product toward the user's skin. Advantageously, this plate 29 is not conductive, in order to avoid irritation or tingling on the user's skin. The plate 29 may be made of a polymer material. Preferably, but not restrictively, the polymer is a thermoplastic such as a polytetrafluoroethylene (PTFE) or a polyoxymethylene (POM). In this embodiment, the first and second electrodes 17, 18 for iontophoresis are made of a composite material. Advantageously, the composite material may be a carbon-filled polymer.

The first and second electrodes 17, 18 may be arranged in various ways above the upper surface 5 of the base 4. In one embodiment, as illustrated on FIGS. 1, 3, 6 and 7, the first electrode 17 is arranged at the center of the base 4. As for the second electrode 18, it is arranged at the periphery of the applicator head 3, more precisely, around the perimeter of the inter-electrode zone 19. The first electrode 17 illustrated has a roughly triangular shape. The second electrode 18, in this embodiment, has a closed contour with a generally triangular shape. In another embodiment, illustrated in FIG. 8, the first and second electrodes 17, 18 for iontophoresis have a rectangular shape. These are arranged parallel to each other and are separated by the inter-electrode zone 19. According to another embodiment illustrated in FIG. 9, the first and second electrodes 17, 18 are rectangular in shape. The electrodes are four in number and they are arranged at a distance from each other. The inter-electrode zone 19 is arranged at the center of the applicator head 3 such that there are, for example, two first electrodes 17 to the left of the inter-electrode zone and two second electrodes 18 to the right of the inter-electrode zone 19. According to yet another embodiment illustrated in FIG. 10, the first electrode 17 has the general shape of a cross with two perpendicular branches forming four edges 32. The first electrode 17 is arranged at the center of the head 3, and in particular at the center of the upper surface 5 of the base 4. Some second electrodes 18, in this case four of them, are arranged at a distance from the first electrode 17 and around the latter. Each second electrode 18 is arranged in line with the extension of an edge 32 of the first electrode 17. The inter-electrode zone 19 separates the first and second electrodes 17, 18. Other configurations of the first and second electrodes 17, 18 are, of course, possible.

In the various embodiments described, the applicator head 3 comprises at least one electrical insulation means 33 which is fluidically interposed between the first electrode 17 and the second electrode 18. This electrical insulation means 33 is configured so as to permit or limit, or even prevent, the passage of electric current between the first electrode 17 and the second electrode 18 via the applicator head 3. In reference to FIGS. 6 and 7, the insulation means 33 is arranged on one of the distribution channels 16. In order to be able to control the circulation of electric current between the first electrode 17 and the second electrode 18, the electrical insulation means 33 is arranged on the distribution channel 16 which leads towards the first electrode 17, between the distribution opening 91 and the outlet 15 of the buffer reservoir 13. In fact, on FIGS. 6 and 7, the first electrode 17 for iontophoresis is situated at the center of the applicator head 3 while the second electrode 18 for iontophoresis surrounds the periphery of the first electrode 17, and in particular, the inter-electrode zone 19.

Advantageously, but not restrictively, the electrical insulation means 33 is situated close to the distribution opening 91 of the distribution channel 16 leading to the first electrode 17 in order to limit as much as possible the leakage currents toward the second electrode 18 via the applicator head.

To permit or limit the passage of current between the first electrode 17 and the second electrode 18 via the applicator head 3, the electrical insulation means 33 is able to be in an open position or a closed position. In the closed position, current circulates only between the first electrode 17 and the second electrode 18, and in the open position, current circulates in a limited manner in the applicator head 3 and in the body 2. The electrical insulation means 33 has a clearance area which, when the electrical insulation means 33 is in the open position, permits the circulation of electric current between the first and the second electrodes 17, 18 and in the distribution channels 16 of the applicator head 3. Nevertheless, this clearance area is so small that the impedance of the path to travel is too great to favor circulation of current via this clearance area. Thus, the electric current circulates almost exclusively in the application interface (skin side) rather than toward the interior of the applicator head 3 and the body 2.

In the open position, the product to be distributed circulates from the body 2 toward the first and second electrodes 17, 18, while in the closed position, the product no longer circulates toward the first electrode 17. Once the product is again extracted from the storage means 84 toward the buffer reservoir 13, the pressure of the product causes the electrical insulation means 33 to open such that the first and second electrode 17, 18 for iontophoresis are supplied with product. The opening pressure of the electrical insulation means 33 is chosen appropriately in relation to the distribution channels 16 supplying the second electrode 18 and the associated pressure loss. Ideally, the pressure loss undergone by the product to be distributed in the passage of the insulation means 33 is equal to the pressure loss of the longer distribution channels 16 supplying the second electrode 18. Alternatively, electrical insulation means 33 may also be arranged on the distribution channels 16 leading to the second electrode 18 for iontophoresis. This advantageously permits balancing the product's circulation toward the first and second electrodes 17, 18 for iontophoresis, and thus optimizing equal supply of product to the first and second electrodes 17, 18 for iontophoresis.

In addition, the insulation means 33 is in the open position when a pressure inside the insulation means 33 reaches a predetermined threshold. Advantageously, but not restrictively, the insulation means 33 is a valve, and preferably, a check valve as illustrated in FIGS. 11 to 13. However, the insulation means 33 may take another form. The valve comprises a body with a first end at which an entry 34 is formed and an opposite second end at which an exit 35 is formed. The exit 35 is in the form of a duck's bill formed of two opposite lips 36 that are elastically deformable. The two lips 36 open if the pressure value inside the valve is at least equal to a predetermined pressure threshold value, and they close when the pressure value inside the valve is lower than the predetermined pressure threshold value. The predetermined pressure threshold value is between 5 and 200 millibars (mbar). Preferably, but not restrictively, the predetermined threshold pressure value is approximately 50 mbar. It should be noted that in the open position, the clearance area of the lips 36 formed at the outlet 35 is very low, and consequently the impedance is high. The maximum clearance area (of opening) of the lips 36 is between 0.2 mm$^2$ and 2.5 mm$^2$. Thus, the circulation of the product to be distributed is possible, but that of the current is limited between the first electrode 17 and the second electrode 18 for iontophoresis via the applicator head 3.

The valve is made of a polymer material, such as silicone.

The applicator head 3 comprises the cap 37 or cover secured to the base 4 to hold the first and second electrodes 17, 18 in position in the applicator head 3. The cap 37 comprises the collar 38 which has a central opening 39 through which the base 4 is received. The first and second electrodes 17, 18 as well as the assembly member (application surface 20) are visible through this central opening 39. The collar 38 has an upper surface 101 which is defined in a plane D. This upper surface 101 forms a support ring whose purpose is to create a volume with a low thickness on the skin. This plane D is roughly parallel to the plane C of the application surface 20 of the inter-electrode zone 19. The plane D is also parallel to the plane B of the first and second electrodes 17, 18 for iontophoresis. The collar 38 of the cap 37 includes in its periphery a side skirt 40 intended to cooperate with the wall 7 of the base 4. In particular, between the side skirt 8 and the wall 7 of the base 4, there is provided a flange 41 on which rests a free end 42 of the side skirt 40. The wall 7 of the base 4 also has blind slots 43 (see FIG. 5) in each of which a ledge 44 is mounted on an inner wall 45 of the side skirt 40 to attach the cap 37 to the base 4. To facilitate the disassembly of the cover 37 of the base 4, the base includes a notch 99 on the wall 7. The notch is situated close to each blind slot 43 and allows the users finger to access the free end 42 of the cover 37.

Between the inner wall 45 of the side skirt 40 of the cap 37 and the wall 7 of the base 4 is arranged a first gasket 46. In order for the first gasket 46 to be held in position, the wall 7 of the base 4 includes a groove 47 extending in the direction of the perimeter of the wall 7. The first gasket 46 has a ring-shaped body. Advantageously, the first gasket 46 is made of an elastically deformable material. This deformable material is preferably a polymer or a copolymer chosen from one of the following: an ethylene propylene diene monomer (EPDM), a fluorocarbon rubber (FPM), a polyacrylic elastomer (ACM), an ethylene-acrylic copolymer (AEM), a hydrogenated nitrile rubber (HNBR), a VITON®, or a butyl.

The applicator head 3 further comprises a connecting member 48 to removably connect the applicator head 3 and the body 2 (see FIG. 5). This connecting member 48 comprises a support part 49 which includes an upper face 50 and a lower face 51 connected by a wall 52. The support part 49 has an opening 54 going through the wall 52 on both sides. This opening 54 communicates with the entrance 14 of the buffer reservoir 13. The support part 49 is equipped with fixing brackets 55, three of them here, which extend from the inner face 51 of the support part 49. The support part 49 is force fit with the inner surface 9 of the side skirt 8 of the base 4. The fixing brackets 55 have roughly a V shape toward each of their free ends 56. These fixing brackets 55 cooperate with a bulge 57 provided at a proximal end 58 of the body 2. The bulge 57 is arranged on an inner surface 60 of the body 2. The wall 52 is provided with a groove 53 extending along the perimeter of the wall 52 and in which a second gasket 61 is installed. The gasket 61 is in contact with the inner surface 9 of the side skirt 8.

Advantageously, the product to be distributed is contained in a cartridge 63 which is removably connected to the body 2 of the device. Thus, when the product is exhausted, the cartridge 63 may easily be replaced or refilled.

In reference to FIG. 14, the cartridge 63 comprises a housing 66 receiving an attaching head 67. The attaching head 67 is inserted through the opening 54 of the connecting member 48 and a portion of the attaching head extends in the buffer reservoir 13. The attaching head 67 is attached in relation to the applicator head 3. A gasket 70 is also housed in a groove 69 of the support part 49 of the connecting member 48. The gasket 70 is fixed in the groove 69 by a stop 30 such that the product to be distributed does not intersect the attaching head 67 of the cartridge 63.

The body 2 comprises at least one extraction means 78 to permit extracting the product in the storage means 84 from the body 2. This means 78 may be manual or motorized. In manual mode, the device may comprise a drive means comprising a portion 83 (see FIG. 1) extending through the opening 77 of the body 2 of the device 1 so that the user can activate it easily. Advantageously, but not restrictively, this drive means 82 comprises a wheel 85.

As a variant, the motorized extraction means 78 comprises a motor (not represented) activating means to permit rotating a distribution mechanism. The motor may be activated via a button accessible on the body 2 of the application device 1. This button is connected to an electronic control circuit 72 to activate the motor.

In the body 2 is also arranged a current generator 71 to permit delivering a low-intensity current to the first and second electrodes 17, 18 arranged in the applicator head 3. The electric current is between 50 microamperes (µA) and 6000 µA. Preferably, but not restrictively, the electric current is approximately 800 µA. The current may be alternating or direct. The electric current generator 71 is controlled by the electronic control circuit 72 installed in the body 2 of the product application device 1 to provide the current. The electronic control circuit 72 is powered by an electric power source 90 that may be a battery or a rechargeable battery on a household power supply grid. Alternatively, the device 1 may comprise an electric power cord (not represented) intended to be connected to the household power supply grid and to power the electronic control circuit 72. To ensure an electrical connection between the current generator 71 and the first and second electrodes 17, 18, these electrodes are each equipped with a pin 73, 73'. The pins 73, 73' and the first and second electrodes 17, 18 are formed of a single part. Each pin 73, 73' (see FIGS. 5 and 14) has a free end 74 accessible from the lower interface of the applicator head 3. In other words, each pin 73, 73' crosses the inter-electrode zone 19, the base 4 and the connecting member 48 on both sides via slits 75, 75' contained by the latter. The pins 73, 73' are thus accessible from the lower face 51 of the connecting member 48 of the applicator head 3. Each pin 73, 73' has a length superior to the lengths of the inter-electrode zone, the base 4 and the connecting member 48. Here, each of the pins 73, 73' has a section in the shape of a backwards L. The body 2 of the device comprises connecting elements 76 which are connected to the current generator 71.

On FIGS. 14 to 16, one connecting element 76 is connected to the anode of the current generator and another connecting element 76 is connected to the cathode of the current generator 71. As such, when the applicator head 3 is connected to the body 2 of the device 1, each pin 73, 73' cooperates with a connecting element 76 and is supplied with electric current.

According to a characteristic of the invention, when the product is distributed, a closed circuit is formed with the user's skin, the first electrode 17 and the second electrode 18. In order to avoid skin microlesions creating sensations of discomfort or even pain in the case of strong intensity or prolonged duration, or to detect a problem with functioning or tolerance, the device may include a temperature probe. Advantageously, this temperature probe is integrated in the applicator head 3 of the application device 1 and connected to the electronic control circuit 72.

We will now describe the functioning of the application device. When the application device is powered up, the electronic control circuit 72 sends an order to the current generator 71 which generates a current at the first and second electrodes 17, 18 for iontophoresis. The user activates the extraction means 78 until the product is extracted from the cartridge 63 and collected in the buffer reservoir 13 as a first step. As a second step, the product under pressure triggers the opening of the valve, when the pressure inside the valve reaches a predetermined value, which permits the product to pass into the distribution channels 16 formed in the base 4. The product then empties into the distribution cavity 92 via the distribution openings 91 toward the first and second electrodes 17, 18. The product going through the perforations 28 of the first and second electrodes 17, 18 to the right of the electric field created is transported deep into the skin following the semicircular arched field lines. The distance reached under the skin is between 2 and 10 mm deep.

The invention is described in the preceding as an example. It is understood that those skilled in the art are able to carry out different embodiment variants of the invention, for example, by combining the various above characteristics taken alone or in combination, without departing from the context of the invention.

The invention claimed is:

1. A device for applying a product to be distributed on skin of a user by iontophoresis, the device comprising:
   a body intended to receive the product to be distributed and comprising an electric current generator; and,
   an applicator head mounted on the body, the applicator head having an upper interface to be applied against the user's skin, the applicator head comprising:
      at least one distribution means for distributing the product to be distributed on the skin;
      a first electrode and a second electrode separated by an inter-electrode zone, the first electrode and the second electrode being arranged, respectively, in a first cavity and a second cavity of the applicator head, the inter-electrode zone being formed by an assembly member that has a bottom part, a side wall and an upper surface, the side wall connecting the bottom part to the upper surface, said assembly member arranged between the first electrode and the second electrode and separating the first cavity in which the first electrode is arranged, from the second cavity, in which the second electrode is arranged, the first electrode and the second electrode being set back from said upper surface of the assembly member so that the upper surface of the assembly member is provided closer to the upper interface than the first electrode and the second electrode, the first electrode and the second electrode arranged to receive an electric current from said generator, and
   a distribution circuit containing distribution channels for distributing the product toward the at least one distribution means, the distribution channels including a first distribution channel having an outlet arranged at a bottom of the first cavity to supply the product in said first cavity and a second distribution channel having an outlet arranged at a bottom of the second cavity to supply the product in said second cavity.

2. The device according to claim 1, wherein the first electrode and the second electrode are situated in a same plane.

3. The device according to claim 2, wherein the upper surface of the assembly member of the inter-electrode zone is situated in a plane parallel to said plane of the first electrode and the second electrode, the plane of the first electrode and the second electrode and the plane of the upper surface of the assembly member of the inter-electrode zone being situated at a predetermined distance from each other.

4. The device according to claim 1, wherein the upper surface of the assembly member of the inter-electrode zone defines an application surface intended to be in contact with the user's skin.

5. The device according to claim 1, wherein the upper surface of the assembly member of the inter-electrode zone has a predetermined minimum distance between the first electrode and the second electrode which is between 5 and 20 mm.

6. The device according to claim 1, wherein the first electrode and the second electrode are arranged downstream from the distribution circuit.

7. The device according to claim 1, wherein the first electrode and the second electrode each have a wall with perforations.

8. The device according to claim 7, wherein the at least one distribution means comprises one or more outlet openings, and wherein the perforations constitute the one or more outlet openings for distributing the product toward the user's skin.

9. The device according to claim 1, further comprising a plate with perforations arranged in the applicator head, the at least one distribution means comprising one or more outlet openings and the perforations constituting the one or more outlet openings for distributing the product toward the user's skin.

10. The device according to claim 1, wherein the product is contained in a cartridge removably connected to the body of the device.

11. The device according to claim 1, wherein the body comprises at least one means for extracting the product from the body toward the applicator head.

12. The device according to claim 1, wherein the applicator head comprises an electrical insulation means which is fluidically interposed between the first electrode and the second electrode, the electrical insulation means being configured so as to permit or prevent passage of the electric current from the first electrode and the second electrode to the body.

13. The device according to claim 12, wherein the electrical insulation means is adapted to be in:
- a closed position in which the electric current circulates only between the first electrode and the second electrode; or,
- an open position in which the electric current circulates between the first electrode and the second electrode and in the distribution channels of the applicator head for distributing the product.

14. The device according to claim 13, wherein the electrical insulation means is in the open position when a pressure inside the electrical insulation means reaches a predetermined threshold.

15. The device according to claim 13, wherein the electrical insulation means is arranged on one of the distribution channels leading to the first electrode.

16. The device according to claim 12, wherein the electrical insulation means is a valve.

17. The device according to claim 1, wherein the first electrode is arranged at a center of the applicator head and the second electrode is arranged toward a periphery of the applicator head.

18. The device according to claim 1, wherein the first electrode and the second electrode are set back from said upper surface of the assembly member of the inter-electrode zone so that the first electrode and the second electrode are not in contact with the user's skin during distribution of the product on the user's skin by iontophoresis.

* * * * *